US006506419B2

(12) United States Patent
Takahashi et al.

(10) Patent No.: US 6,506,419 B2
(45) Date of Patent: Jan. 14, 2003

(54) PROANTHOCYANIDIN-CONTAINING COMPOSITION

(75) Inventors: Tomoya Takahashi; Asako Kobayashi, both of Ibaraki (JP)

(73) Assignee: Kyowa Hakko Kogyo Co., Ltd, Tokyo (JP)

( * ) Notice: Subject to any disclaimer, the term of this patent is extended or adjusted under 35 U.S.C. 154(b) by 0 days.

(21) Appl. No.: 09/811,594

(22) Filed: Mar. 20, 2001

(65) Prior Publication Data

US 2001/0036487 A1 Nov. 1, 2001

(30) Foreign Application Priority Data

Mar. 24, 2000 (JP) ........................................ 2000-083647

(51) Int. Cl.$^7$ ........................... A61K 35/78; A61K 7/18
(52) U.S. Cl. ......................................... 424/732; 424/52
(58) Field of Search ..................... 424/52, 732

(56) References Cited

U.S. PATENT DOCUMENTS

| 6,139,872 A | * 10/2000 | Walsh .......................... 424/464 |
| 6,297,218 B1 | 10/2001 | Morazzoni et al. ............ 514/25 |
| 6,346,547 B1 | 2/2002 | Tzodikov ...................... 514/551 |

FOREIGN PATENT DOCUMENTS

| DE | 198 30 004 | 12/1994 |
| EP | 1 086 693 | 3/2001 |
| JP | A-5-112441 | 5/1993 |
| JP | AS-163131 | 6/1993 |
| JP | 6-336420 | 12/1994 |
| JP | B-8-2819 | 1/1996 |
| JP | 2744572 | 2/1998 |
| JP | 11004811 | * 7/2000 |
| WO | 98/42309 | 10/1998 |
| WO | 99/29331 | 6/1999 |
| WO | 99/66881 | 12/1999 |

OTHER PUBLICATIONS

Database, Derwent Publications Ltd., London, GB, AN 1994–313596 (XP002198360).

* cited by examiner

Primary Examiner—Jon P. Weber
Assistant Examiner—Kailash C. Srivastava
(74) Attorney, Agent, or Firm—Fitzpatrick, Cella, Harper & Scinto

(57) ABSTRACT

A composition and method for stabilizing proanthocyanidin, especially for preventing, for example, its discoloration by oxidative polymerization. The method utilizes (and the composition contains) proanthocyanidin, and an amino acid having a hydroxyl group or a dipeptide containing said amino acid. Also shown is a drink, food, cosmetic or medicament which contains the composition.

14 Claims, No Drawings

PROANTHOCYANIDIN-CONTAINING COMPOSITION

FIELD OF THE INVENTION

This invention relates to a composition which contains proanthocyanidin, as well as to a drink, a food, a cosmetic and a medicament which contain the composition, and a method for stabilizing proanthocyanidin.

BACKGROUND OF THE INVENTION

Proanthocyanidin is a substance which is contained in many plants and is known to have strong antioxidant action. However, it is known that this substance is unstable in the presence of oxygen. That is, oxidative polymerization etc. rapidly occurs in the presence of oxygen, which discolors the proanthocyanidin.

A known method for stabilizing proanthocyanidin in a wine includes admixing a wine with potassium pyrosulfite. A known method for stabilizing proanthocyanidin in an apple juice includes admixing an apple juice with ascorbic acid. Also, JP-A-6-336420 (the term "JP-A" as used herein means an unexamined published Japanese patent application and "JP-B" means an examined published Japanese patent publication) discloses a cosmetic in which sodium hydrogen sulfite, 1-hydroxyethane-1,1-disulfonic acid, and diethylenetriaminepentaacetic acid or phytic acid are employed in order to prevent coloring of proanthocyanidin with passage of time.

In addition, as methods or compositions for stabilizing polyphenol or for preventing their discoloration, (1) JP-B-8-2819 discloses a method for preventing discoloration of polyphenol by mixing a porphyrin-zinc complex and an organic reducing agent, (2) JP-A-5-112441 discloses a cosmetic for the skin in which a polyphenol compound is mixed with a sucrose-higher fatty acid ester, (3) JP-A-5-163131 discloses a cosmetic for the skin in which a polyphenol compound is mixed with an alkyl glucoside and (4) Japanese Patent No. 2,744,572 discloses a method for preventing discoloration of an external skin preparation containing a polyhydric alcohol or saccharides mixed with a polyphenol compound having three or more phenolic hydroxyl groups.

The object of the invention is to provide a method for stabilizing proanthocyanidin, particularly for preventing, for example, its discoloration by oxidative polymerization. The object of the present invention is also to provide a proanthocyanidin-containing composition having excellent stability, as well as a drink, a food, a cosmetic or a medicament which contains the composition.

SUMMARY OF THE INVENTION

The invention relates to the following items (1) to (17).

(1) A composition which comprises proanthocyanidin, and an amino acid having a hydroxyl group or a dipeptide containing the amino acid.

(2) A composition which comprises proanthocyanidin and an amino acid having a hydroxyl group.

(3) A composition which comprises proanthocyanidin and a dipeptide containing an amino acid having a hydroxyl group.

(4) The composition according to the item (1), wherein the concentration of the amino acid having a hydroxyl group or the dipeptide containing the amino acid is within the range of from 0.001 to 1% by weight based on the total composition.

(5) The composition according to any one of the items (1) to (4), wherein the concentration of proanthocyanidin is within the range of from 0.01 to 20% by weight based on the total composition.

(6) The composition according to the item (1), (2), (4) or (5), wherein the amino acid having a hydroxyl group is L-serine or L-threonine.

(7) The composition according to the item (1), (3), (4) or (5), wherein the dipeptide containing an amino acid having a hydroxyl group is glycyl-L-serine.

(8) The composition according to any one of the items (1) to (7), wherein proanthocyanidin is derived from a plant belonging to the genus Vitis, Malus, Hordeum, Diospyros, Cocos, Theobroma, Pinus, Vaccinium, Fragaria, Phaseolus or Arachis.

(9) A composition which comprises the composition according to any one of the items (1) to (8) and an additive suited for a drink.

(10) A composition according to the item (9), wherein the drink is a fruit wine, a fruit juice drink or a health drink.

(11) A composition which comprises the composition according to any one of the items (1) to (8) and an additive suited for a food.

(12) A composition which comprises the composition according to any one of the items (1) to (8) and a cosmetically acceptable carrier.

(13) A composition which comprises the composition according to any one of the items (1) to (8) and a pharmaceutically acceptable carrier.

(14) A method for stabilizing proanthocyanidin, which comprises blending proanthocyanidin with an amino acid having a hydroxyl group.

(15) A method for stabilizing proanthocyanidin, which comprises blending proanthocyanidin with a dipeptide containing an amino acid having a hydroxyl group.

(16) A proanthocyanidin stabilizing agent, which comprises an amino acid having a hydroxyl group.

(17) A proanthocyanidin stabilizing agent, which comprises a dipeptide containing an amino acid having a hydroxyl group.

DETAILED DESCRIPTION OF THE INVENTION

Examples of the amino acid having a hydroxyl group include serine, threonine and tyrosine and the like, of which L-amino acids are preferable. Of these, L-serine and L-threonine are especially preferred. Examples of the dipeptide containing an amino acid having a hydroxyl group include glycylserine, glycylthreonine and glycyltyrosine and the like, of which glycyl-L-serine is preferred.

The amino acid having a hydroxyl group or the dipeptide containing an amino acid having a hydroxyl group may be present in the form of a hydrate or a solvate.

Though the amino acid having a hydroxyl group or the dipeptide containing an amino acid having a hydroxyl group can be synthesized by a known method, it can also be purchased as a commercial product.

As the proanthocyanidin, a group of compounds in which two or more of the flavan-7-ol derivative represented by the following formula (I) are bonded together can be exemplified. In the proanthocyanidin, a carbon atom of one of the flavan-7-ol derivatives and the same or different carbon atom of another one of the flavan-7-ol derivatives may be bonded together, for example, through a single bond or an ether bond (via an oxygen atom), etc. In the case of an ether bond, such may be effected via a portion of hydroxyl group of the flavan-7-ol derivative. Of course, the carbon atom concerned in this bonding may be any carbon atom which can be utilized. Also, irrespective of the bond utilized, the structural units of the flavan-7-ol derivatives may be the same or different from each other.

Desirable proanthocyanidins preferably have from 2 to 10, more preferably from 2 to 4, structural units of a flavan-7-ol derivative.

According to the invention, various types of proanthocyanidin may be used alone or as a mixture of two or more.

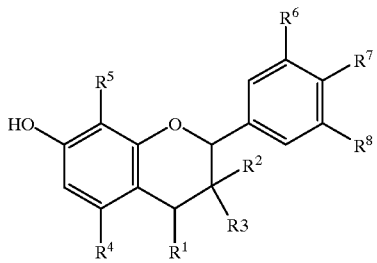
(I)

In formula (I), $R^2$ and $R^3$ are independently a hydrogen atom, a hydroxyl group, a galloyloxy group or a glucopyranosyloxy group, and $R^1$, $R^4$, $R^5$, $R^6$, $R^7$ and $R^8$ independently represent a hydrogen atom or a hydroxyl group.

Preferred illustrative examples of the flavan-7-ol derivative represented by the formula (I) include catechin, epicatechin, gallocatechin, epigallocatechin, afzelechin and epiafzelechin.

An example of the binding mode between the flavan-7-ol derivatives in proanthocyanidin is shown by the following formulae (II-a), (II-b) and (II-c).

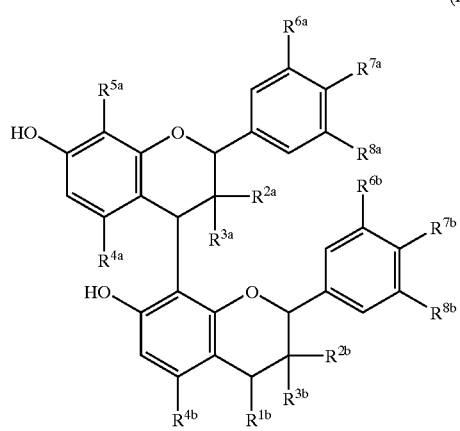
(II-a)

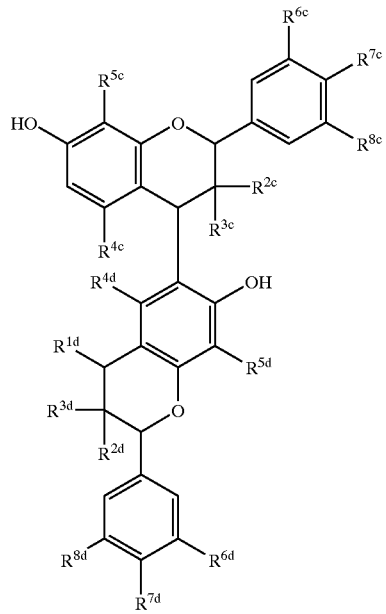
(II-b)

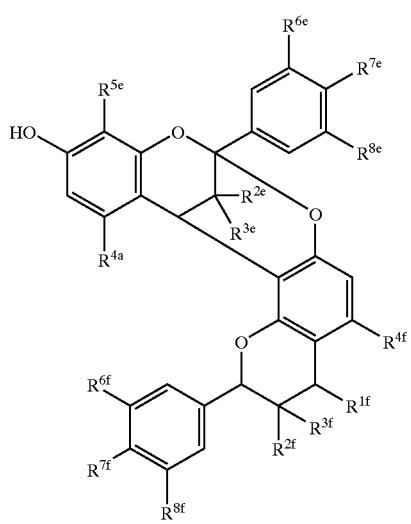
(II-c)

In formulae (II-a, II-b and II-c), $R^{2a}$, $R^{2b}$, $R^{2c}$, $R^{2d}$, $R^{2e}$, $R^{2f}$, $R^{3a}$, $R^{3b}$, $R^{3c}$, $R^{3d}$, $R^{3e}$ and $R^{3f}$ independently represent a hydrogen atom, a hydroxyl group, a galloyloxy group or a glucopyranosyloxy group, and $R^{1b}$, $R^{1d}$, $R^{1f}$, $R^{4a}$, $R^{4b}$, $R^{4c}$, $R^{4d}$, $R^{4e}$, $R^{4f}$, $R^{5a}$, $R^{5c}$, $R^{5d}$, $R^{5e}$, $R^{6a}$, $R^{6b}$, $R^{6c}$, $R^{6d}$, $R^{6e}$, $R^{6f}$, $R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$ and $R^{8f}$ independently represent a hydrogen atom or a hydroxyl group.

Examples of the dimer of the flavan-7-ol derivative include a combined form of epicatechin and catechin such as epicatechin-(4β→8)-catechin, an epicatechin dimer such as epicatechin-(4β→6)-epicatechin or epicatechin-(4β→8)-epicatechin (procyanidin B-2) and a catechin dimer such as catechin-(4α→8)-catechin, and examples of the trimer of the flavan-7-ol derivative include an epicatechin trimer such as epicatechin-(4β→8)-epicatechin-(4β→8)-epicatechin or epicatechin-(4β→8)-epicatechin-(4β→6)-epicatechin, a catechin trimer such as catechin-(4α→8)-catechin-(4α→8)-catechin and a mixed trimer of epicatechin and catechin such as epicatechin-(4β→8)-epicatechin-(4β→8)-catechin.

Compounds in which gallic acid or a saccharide such as glucose or rhamnose is added to the compounds described in the foregoing are also included in the proanthocyanidin in this invention.

Proanthocyanidin exists in various isomer forms such as optical isomers, and all of these isomers and mixtures thereof are also included in the proanthocyanidin in this invention.

Proanthocyanidin is obtained by extracting and purifying it from various plants such as a grape, an apple, a barley, a persimmon, a coconut, a cacao, a pine, a blueberry, a strawberry, an adzuki bean and a peanut. Such plants preferably belong to the genera Vitis, Malus, Hordeum, Diospyros, Cocos, Theobroma, Pinus, Vaccinium, Fragaria, Phaseolus or Arachis. Proanthocyanidin can also be obtained optionally by purification from fermentation products of suitable extracts, such as a wine, an apple wine and a beer.

Its extraction and purification from a plant can be carried out by the following known methods. Suitable parts of a plant such as fruits, seeds, leaves, stems, roots or rootstocks as the starting material are collected at an appropriate season and directly used as the extraction material, or more preferably after first subjecting the collected plant parts to a drying step such as air-drying.

Extraction of proanthocyanidin from the collected extraction material can be carried out in accordance with the known methods [*Chemical & Pharmaceutical Bulletin*, 38, 321 (1990) and 40, 889–898 (1992)]. As discussed therein, the starting material is pulverized or finely cut and then extracted using a solvent. As the extraction solvent, one or more hydrophilic or lipophilic solvent can be used alone, sequentially or together in admixture. Such solvents are preferably selected from solvents such as water, alcohols such as ethanol, methanol and isopropanol, ketones such as acetone and methyl ethyl ketone and esters such as methyl acetate and ethyl acetate. The extraction temperature is generally from 0 to 100° C., preferably from 5 to 50° C.

The extraction time is approximately from 1 hour to 10 days, and the amount of the solvent is generally from 1 to 30 times by weight, preferably from 5 to 10 times by weight, based on the dry material. The extraction step may be carried out by either stirring or soaking and standing. As occasion demands, the extraction step may be repeated 2 or 3 times.

As the purification method of proanthocyanidin (purification method A) from an extract obtained by removing insoluble residue by filtration or centrifugation from the crude extract prepared as above (or from a squeezed liquid of a plant or a sap), any method can be used. Preferable methods include known methods for separation purification of crude drugs. More desirable processes use techniques such as a two-phase solvent partition, column chromatography and/or preparative high performance liquid chromatography, alone or in combination. Examples of the two-phase solvent partition include a method in which oil soluble components and pigments are extracted with a solvent such as n-hexane or petroleum ether and removed, and a method in which the extract is partitioned into a solvent such as n-butanol or methyl ethyl ketone and water to recover proanthocyanidin from the solvent phase. Examples of the column chromatography include ion-exchange column chromatography which uses a carrier such as Amberlite IR-120B or Amberlite IRA-402, absorption column chromatography which uses a carrier such as normal phase silica gel, reverse phase silica gel, Diaion HP-20 or Sepabeads SP-207 and gel filtration which uses a carrier such as Sephadex LH-20. Examples of the preparative high performance liquid chromatography include a method which uses a reverse phase column containing a carrier such as octadecyl silica and a method which uses a normal phase column containing a carrier such as silica gel. Again, these methods can be used as desired alone or in combination and repeatedly.

By this purification method, impurities including water-soluble ionic substances such as salts, nonionic substances such as saccharides and polysaccharides, oil contents and pigments are removed from the crude extract and proanthocyanidin is thereby purified.

Also, proanthocyanidin extracted from grape seeds can be obtained by purifying it in accordance with a method described, for example, in *Acta Derm. Venereol.* (Stockh.), 78, 428 (1998).

As a method for the synthetic production of proanthocyanidin, a production method of an epicatechin or catechin dimer is described in *Journal of the Chemical Society: Perkin Transactions I*, 1535–1543 (1983). Accordingly, various types of proanthocyanidin can be synthesized in accordance with the method described in the document or a modified method thereof.

Alcohol fermentation products of plant extracts containing proanthocyanidin can be obtained by the following known methods. That is, in the case of single fermentation spirits such as a wine and an apple wine, they are produced by subjecting a fruit juice to alcohol fermentation with yeast. For example, in producing a red wine from a grape juice, grapes are pulverized and mixed with an antioxidant and then mixed with from 2 to 5 weight % of yeast, and the mixture is subjected to the main fermentation for 7 to 10 days. Next, this mixture is pressed to remove the rind and precipitate, transferred into a cask equipped with a fermentation bung and then subjected to further fermentation at about 10° C. until the residual sugar becomes 0.2% or less. Thereafter, the lees such as tartar, tannin and protein are filtered off and then the filtrate is stored and aged for several years, thereby producing the wine. Further, in the case of a multiple fermentation type fermentation wine such as a beer, such is produced using cereal starch as the starting material and first carrying out saccharification with amylase and then effecting alcohol fermentation. For example, in producing a beer using a barley as the main material, a malt juice is prepared from a malt and water and then fermented by adding yeast. This is subjected to 10 days of main fermentation at 7 to 10° C., transferred into a storage tank and then subjected to 60 days of after-fermentation at 0 to 2° C. After completion of the after-fermentation, filtration or heat sterilization is carried out to obtain the desired fermentation product.

Regarding the purification method of proanthocyanidin from these alcohol fermentation products, the method similar to that exemplified as the purification method A can be cited.

Illustrative examples of the proanthocyanidin obtained from plants or alcohol fermentation products include proanthocyanidin extracted from grape seeds, a product extracted and purified from a red wine, proanthocyanidin derived from an apple, proanthocyanidin derived from a pine and a purified proanthocyanidin oligomer.

According to the composition of the invention, the amount of proanthocyanidin to be contained is not particularly limited by its use or other conditions, but in the case of a composition for certain uses such as a drink, a food, a cosmetic, a medicament, etc., it is preferably from 0.01 to 20% by weight, more preferably from 0.1 to 10% by weight, based on the total amount of the composition (total weight of the all formulated components).

According to the composition of the invention, the content of the amino acid having a hydroxyl group or the dipeptide containing an amino acid having a hydroxyl group is not particularly limited and can be optionally decided depending on its use or other conditions such as the type of proanthocyanidin, and in the case of a composition for certain uses such as a drink, a food, a cosmetic, a medicament, etc., it is preferably from 0.001 to 1% by weight, more preferably from 0.005 to 0.5% by weight, most preferably from 0.01 to 0.3% by weight, based on the total amount of the composition (total weight of the all formulated components).

The composition of the invention may further contain desirable antioxidants such as sodium hydrogen sulfite, potassium pyrosulfite, ascorbic acid, erythorbic acid or tocopherols.

In addition, the composition of the invention can be used in various applications such as a drink, a food, a cosmetic or a medicament, by optionally adding additives suited for each use.

As the form of the drink of the invention, alcoholic drinks such as a fruit wine, as well as a soft drink, a health drink, a stamina drink, a vitamin drink and a fruit juice drink, can be exemplified.

The drink of the invention can be obtained by mixing an amino acid having a hydroxyl group or a dipeptide containing an amino acid having a hydroxyl group with a proanthocyanidin-containing drink such as (1) a fruit juice drink which is obtained by squeezing a plant material and can be taken as such, such as an apple juice, a grape juice or a blueberry juice, (2) a drink obtained by hot water extraction from a plant material or a processed product thereof, including various teas such as a barley tea, a green tea, an oolong tea, a black tea, a persimmon leaf tea and a boxthorn tea, (3) a drink obtained by carrying out alcohol fermentation of a plant squeezed liquid, including fruit wines such as a grape wine, an apple wine and a blueberry wine and alcohol drinks such as a beer and a froth wine or (4) a drink obtained by soaking a fruit in alcohol and then extracting the extract contents, such as a Chinese quince wine or a plum liquor. Further, soft drinks, health drinks and stamina drinks can be produced by a conventional method by adding, in addition to proanthocyanidin and the amino acid or dipeptide, appropriate additives such as protein, saccharides, fat, trace elements, vitamins, emulsifying agents or spices as occasion demands.

As the form of the food of the invention, food articles such as tablets, capsules, powders, pills, jellies, a frozen food, a powdered food, a sheet-shaped food, a bottled food, a canned food and a retort pouch food and processed forms such as a natural liquid food, a semi-digested nutritious food and a composition nutritious food can be exemplified.

The food of the invention can be produced by a conventional method by adding materials generally used in food, such as protein, saccharides, fat, trace elements, vitamins, emulsifying agents or spices, to proanthocyanidin, and an amino acid having a hydroxyl group or a dipeptide containing an amino acid having a hydroxyl group.

Also as the food of the invention can be exemplified products obtained by processing fruits, such as various types of jam and syruped products of various fruits.

As the form of the cosmetic of the invention, liquid products, gel-like products, emulsion-like products and solid products such as cream can be exemplified.

The cosmetic of the invention can be produced by a conventional method by adding materials generally used in cosmetics, such as solid or semi-solid oils, liquid oils, moisture keeping agents, emollients, surfactants, water-soluble polymers, oil-soluble polymers, organic or inorganic pigments, organic powders, ultraviolet ray absorbents, anti-inflammatory agents, refrigerants, antiseptics, antioxidants, pH-adjusting agents (e.g., a citrate buffer), bactericides, vitamins, crude drugs or crude drug components, skin softening agents, aromatics, pigments, ethanol or purified water, to proanthocyanidin, and an amino acid having a hydroxyl group or a dipeptide containing an amino acid having a hydroxyl group.

As the cosmetic of the invention, face lotions, cosmetic liquids, moisture lotions, milky lotions, creams, packs, hair tonics and shampoos can be exemplified.

As the form of the medicament of the invention, tablets, capsules, powdered preparations, pills, powders, fine subtilaes, granules, syrups and troches can be exemplified.

The medicament of the invention contains proanthocyanidin, an amino acid having a hydroxyl group or a dipeptide containing an amino acid having a hydroxyl group and, as occasion demands, other components effective for the medicament and is prepared in the usual way generally using an excipient. Examples of the excipient include saccharides (e.g., sorbitol, glucose and lactose), dextrin, starch, inorganic substances (e.g., calcium carbonate and calcium sulfate), crystalline cellulose, distilled water, a sesame oil, a corn oil, an olive oil and a cotton seed oil, but any one of other generally used excipients can also be used. In preparing the medicament, additives such as a binder, a lubricant, a dispersing agent, a suspending agent, an emulsifying agent, a diluent, a buffer, an antioxidant and an antibacterial agent may be used.

The invention also provides a method for the stabilization of proanthocyanidin, which comprises blending proanthocyanidin with an amino acid having a hydroxyl group or a dipeptide containing an amino acid having a hydroxyl group, and this method can be carried out by setting conditions such as the blending amount of the amino acid having a hydroxyl group or dipeptide containing an amino acid having a hydroxyl group in accordance with the descriptions regarding the composition of the invention and the drink, the food, the cosmetic and the medicament of the invention.

Also, the invention provides a proanthocyanidin stabilizing agent, which comprises an amino acid having a hydroxyl group or a dipeptide containing an amino acid having a hydroxyl group, and the conditions such as the blending amount of the amino acid having a hydroxyl group or dipeptide containing an amino acid having a hydroxyl group can be set in accordance with the descriptions regarding the composition of the invention and the drink, the food, the cosmetic and the medicament of the invention.

Next, the mode for carrying out the invention is illustratively shown with reference to Examples, Test Examples and Reference Examples.

In the following, (W/W) indicates (weight/weight) and (V/V) indicates (volume/volume).

EXAMPLE 1

The components shown in the following Table 1 were mixed with stirring to dissolve solid substances, thereby producing the compositions 1 to 11 of the invention. Procyanidin B-2 was produced by the method in Reference Example 3.

TABLE 1 (1)

Composition of compositions 1 to 11 [% (W/W)]

| Components | Composition No. | | | | | |
|---|---|---|---|---|---|---|
| | 1 | 2 | 3 | 4 | 5 | 6 |
| L-Serine | 0.03 | 0.06 | 0.10 | 0.30 | | |
| L-Threonine | | | | | 0.03 | 0.06 |
| Glycylserine | | | | | | |
| PB-2 | 1 | 1 | 1 | 1 | 1 | 1 |
| Citric acid | 0.25 | 0.25 | 0.25 | 0.25 | 0.25 | 0.25 |
| Sodium citrate | 0.25 | 0.25 | 0.25 | 0.25 | 0.25 | 0.25 |
| Ethanol | 70 | 70 | 70 | 70 | 70 | 70 |
| Purified water | 28.47 | 28.44 | 28.40 | 28.20 | 28.47 | 28.44 |

PB-2: Procyanidin B-2 (the same shall apply hereinafter)

TABLE 1 (2)

Composition of compositions 1 to 11 [11% (W/W)]

| Components | Composition No. | | | | |
|---|---|---|---|---|---|
| | 7 | 8 | 9 | 10 | 11 |
| L-Serine | | | | | |
| L-Threonine | 0.10 | 0.30 | | | |
| Glycylserine | | | 0.03 | 0.06 | 0.30 |
| PB-2 | 1 | 1 | 1 | 1 | 1 |
| Citric acid | 0.25 | 0.25 | 0.25 | 0.25 | 0.25 |
| Sodium citrate | 0.25 | 0.25 | 0.25 | 0.25 | 0.25 |
| Ethanol | 70 | 70 | 70 | 70 | 70 |
| Purified water | 28.40 | 28.20 | 28.47 | 28.44 | 28.20 |

EXAMPLE 2

The components shown in the following Table 2 were mixed with stirring to dissolve solid substances, thereby producing the compositions 12 to 20 of the invention. Procyanidin B-2 was produced by the method in Reference Example 3.

TABLE 2 (1)

Composition of compositions 12 to 20 [% (W/W)]

| Components | Composition No. | | | | |
|---|---|---|---|---|---|
| | 12 | 13 | 14 | 15 | 16 |
| L-Serine | 0.03 | 0.06 | 0.10 | 0.30 | |
| L-Threonine | | | | | 0.03 |
| Glycylserine | | | | | |
| PB-2 | 1 | 1 | 1 | 1 | 1 |
| Citric acid | 0.25 | 0.25 | 0.25 | 0.25 | 0.25 |
| Sodium citrate | 0.25 | 0.25 | 0.25 | 0.25 | 0.25 |
| Sodium hydrogen sulfite | 0.05 | 0.05 | 0.05 | 0.05 | 0.05 |
| Ethanol | 70 | 70 | 70 | 70 | 70 |
| Purified water | 28.42 | 28.39 | 28.35 | 28.15 | 28.42 |

TABLE 1 (1)-continued

| Components | Composition No. | | | |
|---|---|---|---|---|
| | 17 | 18 | 19 | 20 |
| L-Serine | | | | |
| L-Treonine | 0.06 | 0.10 | 0.30 | |
| Glycylserine | | | | 0.06 |
| PB-2 | 1 | 1 | 1 | 1 |
| Citric Acid | 0.25 | 0.25 | 0.25 | 0.25 |
| Sodium citrate | 0.25 | 0.25 | 0.25 | 0.25 |
| Sodium hydrogen sulfite | 0.05 | 0.05 | 0.05 | 0.05 |
| Ethanol | 70 | 70 | 70 | 70 |
| Purified water | 28.39 | 28.35 | 28.15 | 28.39 |

EXAMPLE 3

The components shown in the following Table 3 were mixed with stirring to dissolve solid substances, thereby producing the compositions 21 to 24 of the invention. Procyanidin B-2 was produced by the method in Reference Example 3.

TABLE 3

Composition of compositions 21 to 24 [% (W/W)]

| Components | Composition No. | | | |
|---|---|---|---|---|
| | 21 | 22 | 23 | 24 |
| L-Threonine | 0.03 | 0.06 | 0.10 | 0.30 |
| PB-2 | 1 | 1 | 1 | 1 |
| Citric acid | 0.25 | 0.25 | 0.25 | 0.25 |
| Sodium citrate | 0.25 | 0.25 | 0.25 | 0.25 |
| Purified water | 98.47 | 98.44 | 98.40 | 98.20 |

EXAMPLE 4

Production of an Apple Juice

A 10 g portion of L-threonine is added to 100 kg of the turbid apple juice obtained in Reference Example 1 to obtain an apple juice bulk which is then packed in paper packing containers to give the final product.

EXAMPLE 5

Production of a Grape Wine

A 10 g portion of L-threonine is added to 100 kg of the casked grape fermentation liquid obtained in Reference Example 2 and uniformly dissolved by stirring the mixture to obtain a product. This is packed in glass containers to give the final product.

EXAMPLE 6

| Production of a jam | |
|---|---|
| Blueberry | 100 kg |
| Granulated sugar | 60 kg |
| Lemon juice | 1 kg |
| L-Serine | 0.03 kg |

(Preparation method)
Granulated sugar is added to washed berries and the mixture is heated for 30 minutes. After cooling, a lemon juice and glycyl-L-serine are added thereto and uniformly mixed. This is packed in glass containers to give the final product.

EXAMPLE 7

| Preparation of a health drink | |
|---|---|
| Grape seed-derived proanthocyanidin (Reference Example 4) | 1.0 g |
| Glycyl-L-serine | 0.1 g |
| Sodium benzoate | 1.0 g |
| Fructose | 10.0 g |
| Essence (fruits mix) | appropriate amount |
| Pigment (blueberry pigment) | appropriate amount |
| Purified water | residue amount |
| Total volume | 1,000 g |

(Preparation method)
The above mixture is uniformly dissolved by stirring, packed in bottles and then subjected to a heat treatment to obtain the final product.

EXAMPLE 8

| Preparation of a face lotion | |
|---|---|
| (Oil phase components) | |
| Perfume (menthol) | 0.05 g |
| Polyoxyethylene (60 mol) hardened castor oil (manufactured by Nippon Emulsion) | 2.0 g |
| 1,3-Butylene glycol | 5.0 g |
| (Water phase components) | |
| Procyanidin B-2 (Reference Example 3) | 0.5 g |
| L-Serine | 0.06 g |
| Glycerol | 5.0 g |
| Methyl paraben | 0.1 g |
| Citric acid | 0.1 g |
| Sodium citrate | 0.2 g |
| Ethanol | 8.0 g |
| Purified water | residue amount |
| Total volume of the oil phase components and water phase components | 100.0 g |

(Preparation method)
The oil phase components and water phase components are uniformly dissolved separately, and the oil phase is added to the water phase with stirring, thereby obtaining the face lotion.

EXAMPLE 9

| Preparation of a milky lotion | |
|---|---|
| (Oil phase components) | |
| Squalane | 4.0 g |
| Wheat germ oil | 2.0 g |
| Monoglyceryl stearate | 1.0 g |
| Polyoxyethylene stearyl ether (manufactured by Nippon Emulsion) | 4.0 g |
| Propyl paraben | 0.1 g |
| (Water phase components) | |
| Procyanidin B-2 (Reference Example 3) | 0.5 g |
| L-Threonine | 0.06 g |

| -continued | |
|---|---|
| Preparation of a milky lotion | |
| Methyl paraben | 0.1 g |
| Propylene glycol | 0.1 g |
| Polyethylene glycol 6000 (manufactured by Nippon Oil & Fats) | 0.2 g |
| 1% Sodium hyaluronate | 5.0 g |
| Purified water | residue amount |
| Total volume of the oil phase components and water phase components | 100.0 g |

(Preparation method)
The oil phase components and water phase components are separately made into uniform state by heating at 80° C., and the water phase is added to the oil phase with stirring, thereby obtaining the milky lotion.

EXAMPLE 10

| Preparation of a hair tonic | |
|---|---|
| (Oil phase components) | |
| Ethanol | 70 g |
| dl-α-Tocopherol acetate | 0.2 g |
| Pantothenyl alcohol | 0.3 g |
| Polyoxyethylene (60 mol) hardened castor oil (manufactured by Nippon Emulsion) | 1.0 g |
| Propylene glycol | 3.0 g |
| Perfume (menthol) | trace amount |
| (Water phase components) | |
| Procyanidin B-2 (Reference Example 3) | 1.0 g |
| L-Serine | 0.06 g |
| Biotin | 0.0001 g |
| Swertiae extract | 3.0 g |
| Citric acid | 0.04 g |
| Sodium citrate | 0.03 g |
| Sodium hydrogen sulfite | 0.1 g |
| Purified water | residue amount |
| Total volume of the oil phase components and water phase components | 100.0 g |

(Preparation method)
The oil phase components and water phase components are separately made into uniform state at room temperature, and the water phase is added to the oil phase with stirring, thereby obtaining the hair tonic.

EXAMPLE 11

| Preparation of tablets | |
|---|---|
| Grape seed-derived proanthocyanidin (Reference Example 4) | 10.0 g |
| Glycyl-L-serine | 1.0 g |
| Lactose | 89.0 g |
| Dry corn starch | 2.0 g |
| Talc | 1.8 g |
| Calcium stearate | 0.2 g |

(Preparation method)
These components are uniformly mixed and made into tablets using a single shot tablet making machine, thereby producing tablets each having a diameter of 7 mm and a weight of 250 mg.

EXAMPLE 12

| Preparation of a Vitamin drink | |
|---|---|
| Grape seed-derived proanthocyanidin (Reference Example 4) | 0.3 g |
| L-Serine | 0.03 g |
| Taurine | 1.0 g |
| Thiamin | 0.001 g |
| Eleutherocock extract (manufactured by Morinaga Milk Industry) | 0.004 g |
| Ascorbic acid | 0.1 g |
| Citric acid | 0.5 g |
| Fructose-glucose syrup (F-55: manufactured by Sanmatsu Kogyo) | 20 g |
| Sodium benzoate | 0.04 g |
| Essence (fruits mix) | appropriate amount |
| Purified water | residue amount |
| Total volume | 100.0 g |

(Preparation method)

These components are uniformly dissolved by stirring, packed in glass containers and then subjected to a heat treatment, thereby obtaining the product.

TEST EXAMPLE 1

Measurement of Changes in Coloration of Proanthocyanidin with the Passage of Time The compositions 1 to 12, 14 to 20 and 22 to 24 obtained in Examples 1 to 3 were stored at 50° C. for 1 week, and then the absorbance of each of the compositions 1 to 12, 14 to 20, 22 to 24 and their control groups was measured at a wave length of 400 nm (optical path length: 1 cm). In this case, the control group means a composition produced using the same components of the respective composition except that the amino acid having a hydroxyl group or the dipeptide containing an amino acid having a hydroxyl group was excluded from each composition.

The results are shown in Tables 4 to 6.

TABLE 4

Changes in coloration after storage at 50° C. for 1 week [70% (w/w) aqueous ethanol solution]

| Substances tested | Absorbance |
|---|---|
| Control group (compositions 1 to 4) | 0.607 |
| Composition 1 | 0.420 |
| Composition 2 | 0.343 |
| Composition 3 | 0.294 |
| Composition 4 | 0.376 |
| Control group (compositions 5 to 8) | 0.679 |
| Composition 5 | 0.360 |
| Composition 6 | 0.252 |
| Composition 7 | 0.187 |
| Composition 8 | 0.188 |
| Control group (compositions 9 to 11) | 0.634 |
| Composition 9 | 0.541 |
| Composition 10 | 0.493 |
| Composition 11 | 0.547 |

TABLE 5

Changes in coloration after storage at 50° C. for 1 week [70% (w/w) aqueous ethanol solution]

| Substances tested | Absorbance |
|---|---|
| Control group (compositions 12 to 15) | 0.284 |
| Composition 12 | 0.248 |
| Composition 14 | 0.231 |
| Composition 15 | 0.265 |
| Control group (compositions 16 to 19) | 0.305 |
| Composition 16 | 0.233 |
| Composition 17 | 0.178 |
| Composition 18 | 0.150 |
| Composition 19 | 0.118 |
| Control group (composition 20) | 0.224 |
| Composition 20 | 0.207 |

TABLE 6

Changes in coloration after storage at 50° C. for 1 week (aqueous solution)

| Substances tested | Absorbance |
|---|---|
| Control group (compositions 21 to 24) | 0.736 |
| Composition 22 | 0.629 |
| Composition 23 | 0.659 |
| Composition 24 | 0.605 |

Based on the above results, it is readily seen that the compositions of the invention undergo less periodical coloration of proanthocyanidin when compared to the compositions of the control groups.

TEST EXAMPLE 2

Stability test of proanthocyanidin

The compositions 12 to 14 and 16 to 19 obtained in Example 2, the composition 22 obtained in Example 3 and their control groups were stored at 50° C. for 1 week, and then the procyanidin B-2 content was measured by high performance liquid chromatography (HPLC) under the following analytical conditions. In this case, the control group means a composition produced using the same components of the respective composition except that only the amino acid having a hydroxyl group was excluded from each composition.

(HPLC analysis conditions)

Column: Inertsil ODS-2 (4.6 mm in diameter×250 mm in length) manufactured by GL Science Mobile phase: acetonitrile/0.05% trifluoroacetic acid (9/91: volume ratio)

Detector: UV 280 nm

Further, the retention ratio of procyanidin B-2 in the table was calculated by the following equation.

Retention ratio of procyanidin B-2=A/B×100 (%)

A: Amount of procyanidin B-2 before the test

B: Amount of procyanidin B-2 after one week

The results of Test Example 2 are shown in Tables 7 and 8.

TABLE 7

Reserved ratio of procyanidin B-2 after storage at 50° C. for 1 week
[70% (w/w) aqueous ethanol solution]

| Substances tested | Retention ratio (%) |
| --- | --- |
| Control group (compositions 12 to 14) | 93.61 |
| Composition 12 | 98.66 |
| Composition 13 | 102.40 |
| Composition 14 | 99.88 |
| Control group (compositions 16 to 19) | 93.52 |
| Composition 16 | 96.22 |
| Composition 17 | 100.68 |
| Composition 18 | 99.65 |
| Composition 19 | 95.80 |

TABLE 8

Reserved ratio of procyanidin B-2 after storage at 50° C. for 1 week
(aqueous solution)

| Substances tested | Retention ratio (%) |
| --- | --- |
| Control group (composition 22) | 94.41 |
| Composition 22 | 99.00 |

Based on the above results, it is readily understood that the compositions of the present invention provide excellent stability of proanthocyanidin in comparison with the compositions of control groups.

REFERENCE EXAMPLE 1

Production of a Turbid Apple Juice

One ton of washed fruits of an apple variety "Fuji" were applied to a crusher and an aqueous solution of 10 kg of 10% ascorbic acid was added thereto. Next, the juice was squeezed using a press and applied to a screen of 60 meshes. Thereafter, this was sterilized at 95° C. for 20 seconds using a flash sterilization machine, immediately cooled and then centrifuged to obtain the turbid apple juice.

REFERENCE EXAMPLE 2

Production of a Casked Grape Fermentation Liquid

Ten tons of fruits of a grape variety "Cabernet Sauvignon" were applied to a crusher, mixed with 800 g of potassium pyrosulfite and then with 3% of yeast, and the mixture was subjected to 10 days of main fermentation at 20° C. Next, this was pressed to remove the rind and precipitate, transferred into a cask equipped with a fermentation bung and then subjected to after-fermentation at 15° C. Thereafter, the lees such as tartar, tannin and protein were filtered off and then the filtrate was stored for 2 years to effect aging.

REFERENCE EXAMPLE 3

Purification Method of Procyanidin B-2
[Epicatechin-(4β→8)-Epicatechin] from an Apple Juice A 21,120 kg portion of an apple juice was applied to a column (60 cm in diameter×88.5 cm in length: 250 liters in volume) packed with Diaion HP-20 resin (manufactured by Mitsubishi Chemical) which had been equilibrated with water, and the column was washed with 1,000 liters of desalted water and 500 liters of a 15% (v/v) aqueous methanol solution. Next, the substance of interest was eluted with 500 liters of a 45% (v/v) aqueous methanol solution. By drying this eluate, 9,450 g of a dried material was obtained.

A 1,465 g portion of this dried material was dissolved in a 25% (v/v) aqueous methanol solution and applied to a column (18 cm in diameter×39.3 cm in length: 10 liters in volume) packed with Sephadex LH-20 (manufactured by Pharmacia) which had been equilibrated with a 25% (v/v) aqueous methanol solution, the column was washed with 20 liters of a 25% (v/v) aqueous methanol solution and 20 liters of a 50% (v/v) aqueous methanol solution in that order, the substance of interest was eluted with 20 liters of a 75% (v/v) aqueous methanol solution and then the resulting eluate was dried to obtain 233 g of a dried material.

A 116 g portion of the dried material was dissolved in desalted water and then separated by preparative high performance liquid chromatography (150 mm×1,000 mm: ODS column, methanol/a 0.0001% aqueous acetic acid solution =12/88). In this manner, 16.5 g of procyanidin B-2 (purity 94% or more) was obtained. Data of $^1$H-NMR, $^{13}$C-NMR and mass spectrometry of the thus obtained procyanidin B-2 coincided with those of a standard preparation. In this connection, the purity of procyanidin B-2 was examined by HPLC under the same analytical conditions described in Test Example 2.

REFERENCE EXAMPLE 4

Purification of Proanthocyanidin from Grape Seeds

Extraction and purification of proanthocyanidin from seeds of a grape variety Chardonnay were carried out in accordance with the method described in Acta Derm. Venereol. (Stockh.), 78, 428 (1998) to obtain grape seed-derived proanthocyanidin having an average polymerization degree of 3.5 and a galloylation ratio of 25% (molar ratio) per proanthocyanidin constituting monomer.

The galloylation ratio and average polymerization degree were calculated in accordance with the method described in Acta Derm. Venereol. (Stockh.), 78, 428 (1998).

While the invention has been described in detail and with reference to specific embodiments thereof, it will be apparent to one skilled in the art that various changes and modifications can be made therein without departing from the spirit and scope thereof.

This application is based on Japanese patent application No. 2000-83647, filed on Mar. 24, 2000, and incorporated herein by reference.

What is claimed is:

1. A composition which comprises proanthocyanidin, and a dipeptide.

2. A composition which comprises proanthocyanidin and a dipeptide containing an amino acid having a hydroxyl group.

3. The composition according to claim 1, wherein the concentration of the dipeptide containing said amino acid is within the range of from 0.001 to 1% by weight based on the total composition.

4. The composition according to any one of claims 1 or 2, wherein the concentration of proanthocyanidin is within the range of from 0.01 to 20% by weight based on the total composition.

5. The composition according to any one of claims 1, 2 or 3, wherein the dipeptide containing an amino acid having an hydroxyl group is glycil-L-serine.

6. The composition according to any one of claims 1, 2 or 3, wherein proanthocyanidin is derived from a plant belonging to the genus Vitis, Malus, Hordeum, Diospyros, Cocos, Theobroma, Pinus, Vaccinium, Fragaria, Phaseolus or Arachis.

7. The composition according to claim 4, wherein proanthocyanidin is derived from a plant belonging to the genus Vitis, Malus, Hordeum, Diospyros, Cocos, Theobroma, Pinus, Vaccinium, Fragaria, Phaseolus or Arachis.

8. The composition according to claim 5, wherein proanthocyanidin is derived from a plant belonging to the genus Vitis, Malus, Hordeum, Diospyros, Cocos, Theobroma, Pinus, Vaccinium, Fragaria, Phaseolus or Arachis.

9. A composition which comprises the composition according to any one of claims 1, 2 or 3 and a comestibly acceptable fluid excipient.

10. The composition according to claim 9, wherein the drink is a fruit wine, a fruit juice drink or a health drink.

11. A composition which comprises the composition according to any one of claim 1, 2 or 3 and a comestibly acceptable solid excipient.

12. A composition which comprises the composition according to any one of claims 1, 2 or 3 and a cosmetically acceptable carrier.

13. A composition which comprises the composition according to any one of claims 1, 2 or 3 and a pharmaceutically acceptable carrier.

14. A method for stabilizing proanthocyanidin, which comprises blending proanthocyanidin with a dipeptide containing an amino acid having a hydroxyl group.

* * * * *